(12) United States Patent
Tomiyama et al.

(10) Patent No.: US 6,278,027 B1
(45) Date of Patent: Aug. 21, 2001

(54) 3-SUBSTITUTED-2-HALOCYCLOHEPTENONE COMPOUNDS AND A METHOD FOR MANUFACTURING SAME

(75) Inventors: Tsuyoshi Tomiyama; Akira Tomiyama, both of Sakaki-machi; Naoto Ueyama, Ueda; Akira Ohno, Sakaki-machi, all of (JP)

(73) Assignee: Kotobuki Pharmaceutical CO LTD, Naganu-Ken (JP)

( * ) Notice: Subject to any disclaimer, the term of this patent is extended or adjusted under 35 U.S.C. 154(b) by 0 days.

(21) Appl. No.: 09/391,385

(22) Filed: Sep. 8, 1999

(30) Foreign Application Priority Data

Sep. 8, 1998 (JP) .................................................. 10-253595

(51) Int. Cl.7 .................................................. C07C 49/105
(52) U.S. Cl. ........................................ 568/375; 548/306.7
(58) Field of Search ........................... 568/375; 548/306.7

(56) References Cited

U.S. PATENT DOCUMENTS

| 2,662,098 | * | 12/1953 | Howard | 568/375 X |
| 3,084,194 | * | 4/1963 | Terborg et al. | 568/375 X |
| 3,320,272 | * | 5/1967 | Sunagawa et al. | 560/375 X |
| 4,057,556 | * | 11/1977 | Bagli et al. | 424/305 |
| 4,749,681 | * | 6/1988 | Buers et al. | 512/8 |
| 5,151,450 | * | 9/1992 | Murakami et al. | 514/690 |

FOREIGN PATENT DOCUMENTS

| 0650360 | * | 2/1993 | (AU) . |
| 59-134745 | * | 8/1984 | (JP) . |
| 61-215341 | * | 9/1986 | (JP) . |

* cited by examiner

Primary Examiner—Floyd D. Higel

(57) ABSTRACT

The present invention relates to compounds of formula (1).

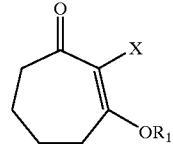

(1)

wherein: $R_1$ is hydrogen atom or lower alkyl group, X is bromine atom or chlorine atom; and which are useful for the preparation of the cycloheptanoides such as cycloheptimidazole derivatives. The compound having formula (1) is obtained in a single pot by the reaction of a trialkylsilylether compound with a dihalocarbene which, in turn, is prepared from the reaction of chloroform or bromoform in the presence of base.

4 Claims, No Drawings

3-SUBSTITUTED-2-HALOCYCLOHEPTENONE COMPOUNDS AND A METHOD FOR MANUFACTURING SAME

BACKGROUND OF THE INVENTION

1. Field of the Invention

This invention relates to novel key intermediates, 3-hydoxy-2-halocycloheptenones and 3-alkoxy-2-halocycloheptenones, which are useful for the synthesis of drug medicine. In detail, this invention relates to preparation of the key intermediates of novel cycloheptimidazole derivatives that have angiotensin II receptor antagonistic activities and are therefore useful for the treatment of hypertension, congestive heart failure and so on.

2. Description of the Prior Art

Many compounds containing cyclohept rings possess potent physiological activities. For example, we proposed cycloheptimidazoles of general formula (6) that have angiotensin II receptor antagonistic activities and are therefore useful for the treatment of hypertension or congestive heart failure. (Japanese Patent laid-open Publication 5-320139, 7-149761 and 8-73454.)

(6)

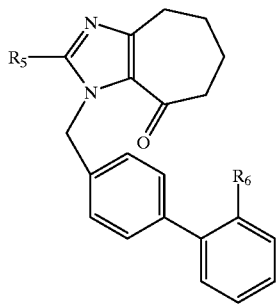

(wherein: $R_5$ is hydrogen atom or lower alkyl group, $R_6$ is carboxyl group, tetrazolyl group) However, the synthetic method of the cycloheptaimidazoles, shown in general formula (6), is unfavorable on an industrial scale because of the following reasons.

1) The starting material, tropolone is expensive.
2) A large number of process steps are needed.
3) This procedure is not applicable to a wide range of cycloheptanoid compounds.

Judging from the application of known method, it is a common concept that 1,3-cycloheptadione (8), prepared from the compound (2), is halogenated at the 2 position of compound (8) to obtain the general formula (1) containing compound (3) and (4).

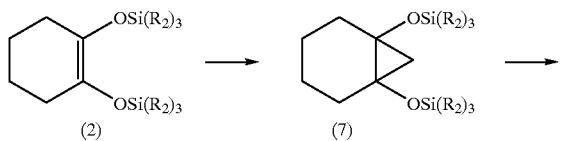

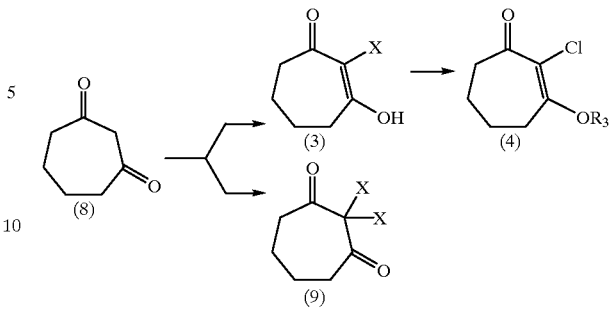

(wherein: $R_2$ and $R_3$ is lower alkyl group, X is bromine atom or chlorine atom.)

In other words Cyclohepta-1,3-dione (8) can be obtained by known method. First, cyclopropanation of compound (2) in the presence of $Et_2Zn$ and $CH_2I_2$ (Simmons-Smith reaction) gives the bicyclic compound (7) (L. Hadjiarapoglou, Synthesis, 525, 1996). Second, ring enlargement of (7) using $FeCl_3$ or periodic acid gives the compound (8) (T. Saegusa, Organic Synthesis 59, 113; M. C. Pirrung, J. Org. Chem. 52, 3606, 1987). Then the halo analogue (3) seems to be prepared in a similar manner as described by R. G. Shepherd (J. Chem. Soc. Perkin Trans. I, 2153,1987), and its etherification affords 2-halo-3-alkoxycyclohept-2-enone(4).

However, Simmons-Smith reaction is not useful industrially because of following reasons.

1) The reaction condition is anhydrous. 2) $Et_2Zn$ is subject to autoignition.

Moreover, the objective compound (3) is not obtained under several conditions for halogenation of the compound (8), and dihalogenation reaction occurs and 2,2-dihalo-1,3-cycloheptandione (9) is obtained as a main product.

Similarly, well-known procedure was not applicable to the synthesis of the compounds (3) and (4). Furthermore, although the compounds (10) (Chem. Abstr. 77, 48038k, 1972 (U.S. Pat. No. 3,658,841)), (11) and (12) (Chem. Abstr. 89, 179583e, 1978 (J. Org. Chem. 43, 4241, 1978)) have already been known, 3-hydroxy-2-halocycloheptenone and 3-alkoxy-2-halocycloheptenone, which are shown as general formula (1), below, are not yet reported and are new compounds.

(10)

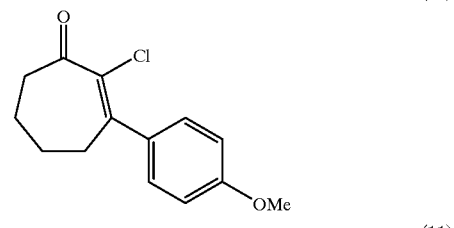

(11)

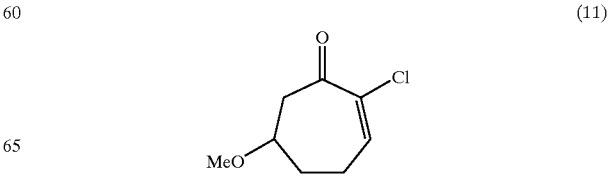

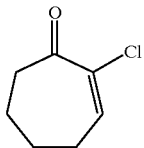

(12)

PROBLEMS TO BE SOLVED BY THE INVENTION

This invention relates to novel key intermediates, useful for the preparation of the cycloheptanoides such as cycloheptimidazole derivatives which are useful for the synthesis of medicine and presents its use for the preparation of the cycloheptimidazoles.

SUMMARY OF THE INVENTION

We have explored to find a practical procedure, of wide range usefulness, for cycloheptanoide compounds. Consequently, we found that 3-hydroxy-2-halocycloheptenone and 3-alkoxy-2-halocycloheptenone were the most suitable intermediates and, at the same time, we found the practical synthetic procedure of these intermediates which is scalable for the industrial scale, and this invention was completed.

Namely, the compounds of the present invention are compounds of general formula (1):

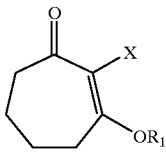

(1)

wherein: $R_1$ is hydrogen atom or lower alkyl group, X is bromine atom or chlorine atom. In this invention, "lower" means straight or branched chain from $C_1$ or $C_5$.

DETAILED DESCRIPTION OF THE INVENTION

The compounds of general (1) such as 3-hydroxy-2-halocycloheptenone and 3-alkoxy-2-halocycloheptenone can be obtained from 1,2-bis(trialkylsilyloxy)cyclohexene (2) which is easily available in a few steps. The synthetic method for preparation of these compounds is shown as follows.

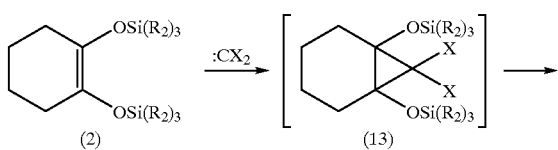

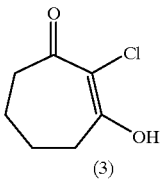 → 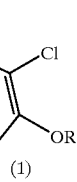

wherein: $R_2$ and $R_3$ are lower alkyl group, X is bromine atom or chlorine atom.

Namely, the compound (13) is obtained by the reaction of 1,2-bis(trialkylsilyloxy)cyclohexene (2) with dihalocarbene which is prepared from chloroform or bromoform in the presence of base such as potassium tert-butoxide. Thus, two reactions, namely a ring chlorination and expansion, proceed in one pot and the compound (13) is subjected to ring expansion to obtain the compound (3) without isolation. This reaction is carried out in an inert organic solvent, such as, heptane, hexane and pentane, at from −40° C. to room temperature.

Above mentioned compound (3) is reacted with alcohol such as methyl alcohol or ethyl alcohol in the presence of acid catalyst to give 3-alkoxy-2-chlorocycloheptenone (compound (4)) or 3-alkoxy-2-bromocycloheptenone. Hydrochloric acid, sulfonic acid, methanesulfonic acid, p-methylbenzene sulfonic acid and ion exchange resin can be used as an acid catalyst. This alkylation is also carried out in the presence of orthoester such as trimethyl orthoformate. In general, this reaction is carried out at a temperature of from 0° C. to room temperature. 1,2-Bis(trialkylsilyloxy)cyclohexene (2) can be prepared according to the reported methods (K. Rublmann., Synthesis, 236, 1971).

Compounds of general formula (4) are as follows: 3-Methoxy-2-chlorocycloheptenone, 3-Methoxy-2-bromocycloheptenone, 3-Ethoxy-2-chlorocyclo-heptenone, 3-Ethoxy-2-bromocycloheptenone and so on.

A compound of general formula (1) can be converted to various cycloheptanoide derivatives. For example, the compounds of general formula (5) are obtained by the reaction of compound (1) with alkylamidine hydrochloride in the presence of base. The compounds of general formula (5) are useful for the synthesis of cycloheptimidazole derivatives which have angiotensin II receptor antagonistic activities.

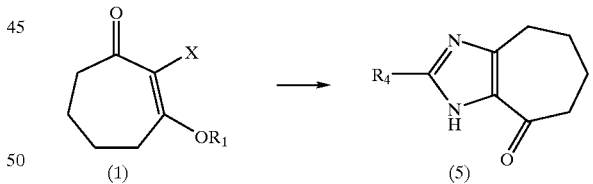

wherein: $R_1$ is hydrogen atom or lower alkyl group, X is bromine atom or chlorine atom, $R_4$ is lower alkyl group.

For example, the compound (1) wherein $R_1$ is lower alkyl group is reacted with butylamidine hydrochloride in the presence of $K_2CO_3$ to give cycloheptimidazole derivatives (5) in which $R_4$ is n-propyl group. In this reaction, 1,4-dioxane or chloroform-$H_2O$ are preferred as solvent. In general, this reaction is carried out at room temperature or under heating conditions.

EXAMPLE

Example 1

2-Chloro-3-hydroxycyclohept-1-one

To a stirred mixture of 67.6 g of 1,2-bis(trimethylsilyloxy)cyclohex-1-ene and 52.1 g of potassium tert-butoxide in 600 mL of pentane, 25.1 mL of chloroform was added over 0.5 h at −20° C. After an additional 0.5 h at room temperature, 10 mL of 10% hydrochloric acid and 30 mL of water was added. After an additional 1 h at room temperature, the mixture was poured into 200 mL of saturated aqueous NaHCO$_3$. The aqueous layer was washed with two portions of ethyl acetate and adjusted to pH 3 using 5% hydrochloric acid solution, followed by extraction with chloroform. The organic solution was washed with brine and dried over Na$_2$SO$_4$, filtered and the solvent was evaporated in vacuo, to give 22 g of the title compound.

MS(m/z): 162 (M$^{+2}$), 160 (M$^+$), 97, 84, 76, 55. $^1$H-NMR (CDCl$_3$) δ 1.97–2.00 (4H, m), 2.37–2.60 (4H, m), 3.60 (2H, s).

Example 2

2-Chloro-3-methoxycyclohept-1-one

A mixture of 5.0 g of 2-chloro-3-hydroxycyclohept-1-one, 5.0 mL of trimethyl orthoformate, and 30 mL of methanol was stirred in the presence of IR 120H ion-exchange resin (0.5 g, pre-washed with methanol) at room temperature. After 3 h the mixture was filtered and filtrate was extracted with ethyl acetate. The organic solution was washed with saturated aqueous NaHCO$_3$, brine and dried over Na$_2$SO$_4$, filtered and the solvent was evaporated in vacuo, to give 2.8 g of the title compound.

MS(m/e): 176 (M$^{+2}$), 174 (M$^+$), 145, 118,97, 61; IR cm$^{-1}$(KBr): 2932, 1653. 1578, 1248, 1224. $^1$H-NMR (CD$_3$OD) δ 1.86 (4H, m), 2.19 (4H, q, J=5.3 Hz), 2.76 (2H, q, J=5.3 Hz), 3.94 (3H, s).

Example 3

2-Propyl-4,5,6,7-tetrahydrocycloheptimidazole-8-one

A solution of 3.7 g of butylamidine hydrochloride and 8.4 g of K$_2$CO$_3$ in 1,4-dioxane, maintained at reflux condition was treated dropwise with a solution of 3.7 g of 2-chloro-3-methoxycyclohept-1-one in 1,4-dioxane. After 2 h the mixture was cooled to room temperature, followed by extraction with ethyl acetate. The organic solution was washed with water, brine and dried over Na$_2$SO$_4$, filtered and concentrated. The crude product was dissolved in toluene, followed by extraction with 10% aqueous NaOH. The aqueous solution was acidified to pH 5.0 with 10% hydrochloric acid and extracted with ethyl acetate. The organic solution was concentrated, followed by acidification with, ethanol which is saturated by hydrochloric acid, and the solvent was removed in vacuo. The residue was recrystallized from ethyl alcohol-diethyl ether to give 3.1 g of title compound.

MS(m/z): 192 (M-HCl)$^+$, 164,131, 95,67. $^1$H-NMR (CD$_3$OD) δ (3H, t, J=6.3 Hz), 1.70–1.82 (2H, m), 2.00 (4H, m), 2.68–2.72 (4H, m), 2.98 (2H, t, J=6.3 Hz).

EFFECTIVENESS OF THE INVENTION

The novel compounds of this invention, 3-hydoxy-2-halocycloheptenone and 3-alkoxy-2-halocycloheptenone, are key synthetic intermediates of cycloheptanoido derivatives. For example, cycloheptimidazol derivatives can be synthesized by using 3-alkoxy-2-halocycloheptenone easily. The compounds of the present invention can be snthesized easily by a short process, and this invention has the advantage that the compounds can be obtained in practical scale with no use of heavy metals and hazardous reagents which present a risk to environmental sanitation.

This invention relates to novel key intermediates, the cycloheptanoide compounds such as cycloheptimidazol derivatives, and their use for the production method of the cycloheptimidazole derivatives.

What is claimed is:

1. A compound having formula (1)

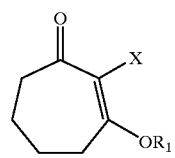

(1)

wherein: R$_1$ is hydrogen atom or lower alkyl group;
X is bromine atom or chlorine atom.

2. A method for preparation of a 3-hydroxy-2-halocycloheptenone compound having formula (3),

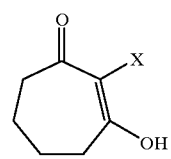

(3)

wherein: X is bromine atom or chlorine atom,
comprising reacting a compound of formula (2)

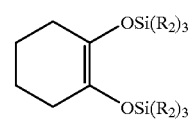

(2)

wherein: R$_2$ is lower alkyl group,
with bromoform or chloroform in the presence of base.

3. A method for preparation of a 3-alkoxy-2-halocycloheptenone compound having formula (4),

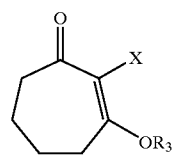

(4)

wherein: R$_3$ is lower alkyl group;
X is bromine atom or chlorine atom,
comprising reacting a compound of formula (3),

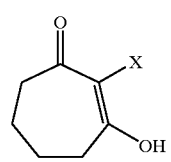

(3)

with lower alkyl alcohol.

4. A method for preparation of a 3-alkoxy-2-halocycloheptenone compound having formula (4),

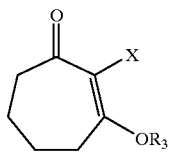
(4)

wherein: R₃ is lower alkyl group;
X is bromine atom or chlorine atom,
comprising reacting a compound of formula (2)

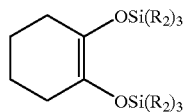
(2)

wherein: $R_2$ is a lower alkyl group, with chloroform or bromoform in the presence of a base, to prepare a compound of formula (3)

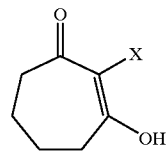
(3)

and reacting the compound of formula (3) with lower alkyl alcohol to produce the compound of formula (4).

* * * * *